United States Patent
Ojima et al.

(10) Patent No.: US 9,238,786 B2
(45) Date of Patent: Jan. 19, 2016

(54) TRANSLUCENT FRAGRANCE COMPOSITION

(75) Inventors: Koujiro Ojima, Yokohama (JP); Tooru Sakura, Yokohama (JP); Michel Sabadie, Ormes (FR); Benedicte Race, Ormes (FR); Karine De Chabannes, Ormes (FR)

(73) Assignees: Shiseido Company, Ltd., Tokyo (JP); Shiseido International France S.A.S., Paris (FR)

( * ) Notice: Subject to any disclaimer, the term of this patent is extended or adjusted under 35 U.S.C. 154(b) by 120 days.

(21) Appl. No.: 14/114,557

(22) PCT Filed: May 1, 2012

(86) PCT No.: PCT/JP2012/061525
§ 371 (c)(1), (2), (4) Date: Oct. 29, 2013

(87) PCT Pub. No.: WO2012/150705
PCT Pub. Date: Nov. 8, 2012

(65) Prior Publication Data
US 2014/0066358 A1 Mar. 6, 2014

(30) Foreign Application Priority Data
May 4, 2011 (EP) .................. PCT/EP2011/057161

(51) Int. Cl.
*C11B 5/00* (2006.01)
*A61Q 13/00* (2006.01)
*A61K 8/34* (2006.01)
*A61K 8/81* (2006.01)
*A61K 8/894* (2006.01)

(52) U.S. Cl.
CPC ................ *C11B 5/0092* (2013.01); *A61K 8/34* (2013.01); *A61K 8/8111* (2013.01); *A61K 8/894* (2013.01); *A61Q 13/00* (2013.01)

(58) Field of Classification Search
CPC .............................. A61Q 13/00; C11B 5/0092
USPC ........................................................... 512/2
See application file for complete search history.

(56) References Cited

U.S. PATENT DOCUMENTS

| | | | |
|---|---|---|---|
| 5,770,112 A * | 6/1998 | Omura et al. .................. 516/20 |
| 2003/0012752 A1 | 1/2003 | Bara | |
| 2006/0210508 A1 | 9/2006 | Gamez-Garcia | |
| 2007/0128232 A1 | 6/2007 | Rahse | |
| 2010/0080832 A1 | 4/2010 | Nagare | |
| 2011/0195037 A1 | 8/2011 | Schmidt | |
| 2011/0318295 A1 | 12/2011 | Shimizu et al. | |
| 2013/0093110 A1 | 4/2013 | Araki | |
| 2014/0044761 A1 * | 2/2014 | Lei et al. ....................... 424/401 |

FOREIGN PATENT DOCUMENTS

| | | |
|---|---|---|
| EP | 0782882 A1 | 7/1997 |
| EP | 2149362 A1 | 2/2010 |
| EP | 2425813 A1 | 3/2012 |
| FR | 2786408 A1 | 6/2000 |
| JP | 3417567 | 6/2003 |
| JP | 2007-513222 | 5/2007 |
| JP | 2010-116354 | 5/2010 |
| JP | 2010-173999 | 8/2010 |
| JP | 2010-254632 | 11/2010 |
| WO | 0247606 | 6/2002 |
| WO | 2005041918 | 5/2005 |
| WO | 2008/143140 | 11/2008 |
| WO | 2010046832 | 4/2010 |
| WO | 2010/086948 A1 | 8/2010 |

OTHER PUBLICATIONS

Patent Abstract and partial translation for JP Publication No. 2010-116354 published May 27, 2010, 13 pages.
Patent Abstract and partial translation for JP Publication No. 2010-173999 published Aug. 12, 2010, 13 pages.
Patent Abstracts of Japan, JP 2010-116354, 16 pages.
Patent Abstracts of Japan, JP 2010-173999, 17 pages.
International Search Report, PCT/JP2012/061525, 2 pages.
Notification of Transmittal of Translation of the International Preliminary Report on Patentability, PCT/JP2012/061525, 6 pages.
Extended European Search Report dated Feb. 24, 2015 issued in the corresponding European patent application No. 12780014.2.

* cited by examiner

*Primary Examiner* — Ling Choi
*Assistant Examiner* — Lanee Reuther
(74) *Attorney, Agent, or Firm* — Rankin, Hill & Clark LLP

(57) ABSTRACT

The present invention provides an alcohol-based stable and translucent fragrance composition containing a large amount of perfume. The fragrance composition of the present invention is a composition in which the total amount of (a) silicone oil and (b) α-olefin oligomer that is a hydrogenated trimer, tetramer, pentamer, and/or hexamer of α-olefin having 4 to 12 carbon atoms is 2 to 12% by mass in the composition, and the mass ratio of (b)/(a) is 0.1 to 0.7; the amount of (c) polyether-modified silicone with respect to (b) α-olefin oligomer is 2 to 10 times in mass; the amount of (d) perfume is 3 to 30% by mass in the composition; the amount of (e) lower alcohol having 1 to 4 carbon atoms is 50% by mass or more in the composition; the amount of (f) water is 3.5 to 15% by mass in the composition; and the L value of the composition is 70 to 95 provided the L value is a percentage (%) of strength of a transmitted light compared with a strength of an incident light.

2 Claims, No Drawings

TRANSLUCENT FRAGRANCE COMPOSITION

RELATED APPLICATIONS

This application claims the priority of International Application PCT/EP2011/057161 filed on May 4, 2011, which are incorporated herein by reference.

FIELD OF THE INVENTION

The present invention relates to a fragrance composition, and in particular to an alcohol-based translucent fragrance composition with an excellent stability.

BACKGROUND OF THE INVENTION

As a fragrance composition such as parfum and eau de cologne, eau de toilette, and eau de parfum, a transparent alcohol solution in which 1 to 30% by mass of perfume is dissolved in a large amount of ethanol has been widely used.

Meanwhile, in products such as cosmetics, the appearance has become one of the important factors for consumer choice. Thus, if a luxurious and new appearance, such as a translucent appearance, is provided with a fragrance composition, the competitiveness of the product can be enhanced.

However, as a fragrance composition contains a large amount of alcohol as well as a large amount of perfume in terms of aromaticity, usability, and so on, it has been difficult to obtain a stable translucent fragrance composition.

Patent Literature 1 describes an oil-in-alcoholic water emulsion in which the oil phase is homogenously and stably dispersed in the outer phase which is mainly comprised of lower alcohol. This emulsion contains 50% by weight or more of lower alcohol such as ethanol, and it further contains, as essential components, oil, water, and as an emulsifier, a specific polyether-modified silicone emulsifier. Patent Literature 1 also describes a hair cosmetic which is an oil-in-alcoholic water emulsion containing an adequate amount of perfume. However, the amount of perfume in a conventional hair cosmetic is generally only 1% by mass or less, and typically only 0.2% by mass or less in the cosmetic.

Since a perfume is one of oil ingredients, the present inventors tried to prepare an alcohol-based fragrance composition containing a large amount of perfume by applying the technique of Patent Literature 1. However, when a perfume was used instead of oil, a composition became transparent, and thus it was very difficult to obtain a translucent stable fragrance composition.

A PRIOR-ART LITERATURE

Patent Literature

Patent Literature 1: Japanese Patent No. 3417567

DISCLOSURE OF THE INVENTION

Problem to be Solved by the Invention

The present invention was made in view of the background art, and an object of the invention is to provide an alcohol-based stable and translucent fragrance composition containing a large amount of perfume.

Means to Solve the Problem

As a result of the diligent studies by the present inventors, they found that an alcohol-based stable and translucent fragrance composition containing a large amount of perfume can be easily obtained by using specific composition, thus leading to completion of the present invention.

The translucent fragrance composition according to the present invention comprises:
  (a) a silicone oil;
  (b) α-olefin oligomer which is a hydrogenated trimer, tetramer, pentamer, and/or hexamer of α-olefins having 4 to 12 carbon atoms;
  (c) a polyether-modified silicone represented by the following formula (1);
  (d) a perfume;
  (e) a lower alcohol having 1 to 4 carbon atoms; and
  (f) water;
wherein the total amount of (a) silicone oil and (b) α-olefin oligomer is 2 to 12% by mass in the composition, and the mass ratio of (b)/(a) is 0.1 to 0.7;
  the amount of (c) polyether-modified silicone with respect to (b) α-olefin oligomer is 2 to 10 times in mass;
  the amount of (d) perfume is 3 to 30% by mass in the composition;
  the amount of (e) lower alcohol is 50% by mass or more in the composition;
  the amount of (f) water is 3.5 to 15% by mass in the composition; and
  the L value of the composition is 70 to 95 provided the L value is a percentage (%) of strength of a transmitted light compared with a strength of an incident light.

$$R-SiO-\left[SiO\right]_m-\left[SiO\right]_n-Si-R \quad (1)$$

(with R substituents and A substituent as shown)

In the formula (1), A is a polyoxyalkylene group represented by the formula $-C_3H_6O(C_2H_4O)_a(C_3H_6O)_bR'$, wherein R' is a group selected from the group consisting of a hydrogen atom, an acyl group having 1-10 carbon atoms, and an alkyl group having 1 to 4 carbon atoms, a is any integer of 5 to 50, and b is any integer of 5 to 50. Rs are respectively methyl or phenyl groups, m is any integer of 50 to 1,000, and n is any integer of 1 to 40.

Also, the present invention provides the translucent fragrance composition wherein the lower alcohol is ethanol.

Effect of the Invention

According to the present invention, an alcohol-based translucent fragrance composition containing a large amount of perfume can be obtained, and the composition is excellent in stability.

Mode for Carrying Out the Invention (a) Silicone Oil

For the silicone oil used in the present invention, any silicone oil generally contained in cosmetics and so on can be used. Examples of such silicone oils include linear polysiloxanes such as dimethylpolysiloxane, methylphenylpolysiloxane, and diphenylpolysiloxane; cyclic polysiloxanes such as decamethylcyclopentasiloxane and dodecamethylcyclohexasiloxane; silicon resin forming three-dimensional network structure; silicone rubber; various kinds of modified polysiloxanes such as amino-modified polysiloxanes, polyether-modified polysiloxanes, alkyl-modified polysiloxanes, and fluorine-modified polysiloxanes. Preferable examples of silicone oils in the present invention include linear polysiloxanes and cyclic polysiloxanes.

(b) α-Olefin Oligomer

α-Olefin oligomer is a hydrocarbon which has high molecular mass (generally, the average molecular mass of 300 or more) and is liquid at ordinary temperature.

The α-olefin oligomer used in the present invention is a hydrogenated trimer, tetramer, pentamer and/or hexamer (preferably, a trimer, a tetramer, and/or a pentamer) of linear α-olefin having 4 to 12 carbon atoms (preferably, 6 to 12 carbon atoms, more preferably, 8 to 12 carbon atoms), that is, a branched saturated hydrocarbon which is obtained by hydrogenation of terminal double bonds after polymerization of the α-olefin. Such an α-olefin oligomer can be synthesized by a known method. But, a commercial product also can be used. For example, "Syncelane 4" (Nikko Chemicals Co. Ltd), "Nomcoat HP-30" (The Nisshin Oillio Group Ltd.), and so on can be used.

In the fragrance composition of the present invention, the amount of α-olefin oligomer with respect to silicone oil is preferably 0.1 times in mass or more, and more preferably 0.2 times in mass or more. It is also preferably 0.7 times in mass or less, and more preferably 0.6 times in mass or less. When the amount of α-olefin oligomer with respect to silicone oil is too small, the composition may become transparent. When it is too large, the emulsification may not be sufficient to fail to obtain the stable translucent composition.

The total amount of (a) silicone oil and (b) α-olefin oligomer is preferably 2% by mass or more, and more preferably 4% by mass or more, in the fragrance composition of the present invention. It is also preferably 12% by mass or less, and more preferably 10% by mass or less. When the total amount of (a) silicone oil and (b) α-olefin oligomer is too small, the composition may become transparent. When it is too large, the emulsification may not be sufficient to fail to obtain the stable translucent composition.

(c) Polyether-Modified Silicone

The polyether-modified silicone used in the present invention is represented by the following formula (1).

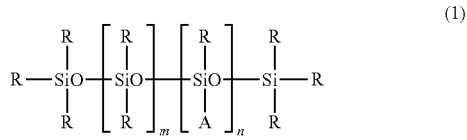
(1)

In the formula (1), Rs are methyl or phenyl groups, m is any integer of 50 to 1,000, and n is any integer of 1 to 40.

A is a polyoxyalkylene group represented by the formula —$C_3H_6O(C_2H_4O)_a(C_3H_6O)_bR'$.

R' is a group selected from the group consisting of a hydrogen atom, an acyl group having 1 to 10 carbon atoms, and an alkyl group having 1 to 4 carbon atoms, a is any integer of 5 to 50, and b is any integer of 5 to 50.

Examples of the acyl groups having 1 to 10 carbon atoms for R' include saturated or unsaturated acyl groups, and the specific examples include formyl, acetyl, propionyl, butyryl, acryloyl, benzoyl, and toluoyl groups. Specific examples of the alkyl groups having 1 to 4 carbon atoms include methyl, ethyl, i-propyl, n-propyl, t-butyl, and n-butyl groups.

When a or b in the polyoxyalkylene group is less than 5, the polyether-modified silicone no longer shows a sufficient surface-active effect. When a or b exceeds 50, the obtained composition becomes sticky.

The amount of polyoxyalkylene group in the molecule is not limited in particular, and it is desired that the amount of polyoxyalkylene group exceed 20% by weight in the total molecular mass. This is because, when the amount of polyoxyalkylene group is 20% by weight or less in the total molecular mass, the effect of polyether-modified silicone decreases significantly, and the stability may be insufficient.

Also, m is any integer of 50 to 1,000, and n is any integer of 1 to 40. This is because the stability is poor when m is less than 50 and n is less than 1, and because the obtained composition becomes sticky when m exceeds 1,000 and n exceeds 40. In addition, the ratio of m:n is preferably 200:1 to 5:1, and particularly preferably 60:1 to 15:1.

The molecular mass and the viscosity at 25° C. of polyether-modified silicone used in the present invention are not limited in particular. However, in terms of forming particularly stable emulsion and providing a light feeling, it is desired that the viscosity of 50 mass % solution of the polyether-modified silicone in octamethyltetrasiloxane or isoparaffin is in the range of 1,000 to 100,000 cps.

The amount of polyether-modified silicone with respect to α-olefin oligomer is preferably 2 times in mass or more, and more preferably 3 time in mass or more. It is also preferably 10 times in mass or less, and more preferably 9 times in mass or less, with respect to α-olefin oligomer. When the amount of polyether-modified silicone with respect to α-olefin oligomer is too small, the emulsification may not be sufficient to fail to obtain the stable translucent composition. When it is too large, the composition may become transparent.

(d) Perfume

The perfume used in the present invention is not limited in particular, and any perfume generally used in cosmetics, pharmaceuticals, fragrances, and so on can be used. The examples include animal-based, plant-based, and mineral-based natural and synthetic perfumes.

The amount of perfume is preferably 3% by mass or more, and more preferably 5% by mass or more, in the composition of the present invention. It is also preferably 30% by mass or less, and more preferably 20% by mass or less. When the amount of perfume is too small, a sufficient scent cannot be obtained, and the composition may become transparent. When perfume is contained excessively, the scent may become too strong, the composition may become sticky, the transparency may increase, and also the amount of the other components is limited.

(e) Lower Alcohol

In the present invention, lower alcohol is a main component in the continuous phase of the fragrance composition, and is contained in 50% by mass or more in the composition in terms of perfume aromaticity, usability, and so on.

Examples of the lower alcohol used in the present invention include monovalent alcohols having 1 to 4 carbon atoms, and ethanol is preferably used considering the safety.

When iso-propanol, n-propanol, tert-butanol, or sec-butanol is used in the composition, it is desired to be used in combination with ethanol because these alcohols have too strong hydrophobicity.

(f) Water

The amount of water is preferably 3.5% by mass or more, and more preferably 4% by mass or more, in the fragrance composition of the present invention. It is also preferably 15% by mass or less, and more preferably 13% by mass or less. When the amount of water is too small, the composition may become transparent. When it is too large, the composition may become while like milk, and the stability may decrease.

The fragrance composition of the present invention is preferably prepared, for example, in the following method:

(i) (a) silicone oil, (b) α-olefin oligomer, (c) polyether-modified silicone, and (d) perfume are mixed and dissolved with a portion of (e) lower alcohol at room temperature (Parts B);

(ii) the rest of (e) lower alcohol and (f) water are mixed and dissolved at room temperature (Parts A); and (iii) Parts A and B are mixed to obtain a fragrance composition.

According to such a method, the translucent fragrance composition, which is a stable microemulsion, can be easily obtained only by mixing and stirring Parts A and B with a stirrer or the like at room temperature, and it does not require heating or any emulsification equipments.

In the step (i), it is preferred that Parts B be solubilized so as to become a transparent one-phase solution. Though Parts B contains a high-viscosity polyether-modified silicone, the use of a part of (e) lower alcohol makes the viscosity of Parts B low. Only by mixing such Parts B with Parts A at room temperature, the microemulsion with dispersed emulsion particle size of 1 μm or less can be easily formed without particular mechanical emulsification, as the translucent fragrance composition with an excellent stability (dispersion phase: oil phase, continuous phase: hydrous-ethanol phase).

In the present invention, when ingredients other than the essential components are to be contained, they can be suitably incorporated in Parts A or B depending on their affinity to prepare the fragrance composition. Generally, lipophilic components can be incorporated in Parts B, and hydrophilic components in Parts A.

In the fragrance composition of the preset invention, the L value of the composition, which is a percentage (%) of strength of transmitted light compared with strength of incident light can be used as the index of translucency. The larger the L value of composition is, the more transparent the composition is. The smaller the L value is, the more white turbid the composition is. In the present invention, the L value is as measured in the examples described below.

The L value of the translucent fragrance composition of the present invention is 70 to 95, and preferably 75 to 90. The composition with the L value of less than 70 is apparently white turbid and lacks luxurious impression in appearance. On the other hand, when the L value exceeds 95, the composition is highly transparent and also lacks luxurious impression in appearance, resulting in being hardly different in appearance from the conventional products.

In the fragrance composition of the present invention, in addition to the essential components, other ingredients which are generally contained in fragrance compositions or which can be contained in cosmetics, quasi drugs, pharmaceuticals, and so on can be contained so far as the effect of the present invention is not undermined. Examples of such components include oils other than silicone oil and α-olefin oligomer, UV absorbers, whitening agents, surfactants, moisturizers, polyhydric alcohols, vitamins, thickeners, film forming agents, antioxidants, and various kinds of drugs.

The fragrance composition of the present invention is preferably used as fragrance cosmetics such as parfum, eau de parfum, eau de toilette, and eau de cologne. It is also usable as air-freshener for domestic use.

EXAMPLES

The present invention will be further illustrated in the following examples. However the present invention is not limited thereto. Unless otherwise noted, the amount is represented as mass %. The evaluation method is as follows.

(Appearance)

The appearance of each sample immediately after preparation was observed by the naked eye.

(L Value)

A quartz glass cell (the optical path length is 10 mm) is filled with a sample without dilution and transmittance was determined at 20° C. by an integrating sphere spectrophotometer (GRETAG MACBETH CE7000A).

Specifically, the sample was irradiated by light evenly from all the angles using the integrating sphere. L value was obtained as a percentage (%) of strength of transmitted light that was received in a normal direction to the sample, compared with strength of the incident light.

(Stability)

The appearance of each sample which had been preserved at room temperature (about 20° C.) for one month was observed by the naked eye and evaluated as follows.

O: The change in appearance such as separation was not observed.

Δ: The change in appearance such as separation was hardly observed.

X: The change in appearance such as separation was observed.

TABLE 1

| | Sample | | | | |
|---|---|---|---|---|---|
| | 1 | 2 | 3 | 4 | 5 |
| <Parts A> | | | | | |
| Ion exchanged water | 3 | 3 | 3 | 3 | 3 |
| 96% Ethanol | 62 | 67 | 62 | 62 | 62 |
| <Parts B> | | | | | |
| 96% Ethanol | 10 | 10 | 10 | 10 | 10 |
| Polyether-modified silicone *1 | 10 | 10 | 10 | 10 | 10 |
| Perfume *2 | 10 | 10 | 10 | 10 | 10 |
| α-Olefin oligomer *4 | 1 | 0 | 0 | 5 | 0 |
| Dimethylpolysiloxane (6 mPa · s) | 4 | 0 | 5 | 0 | 4 |
| Isoparaffin *3 | 0 | 0 | 0 | 0 | 1 |
| Total | 100 | 100 | 100 | 100 | 100 |
| Appearance | Translucent | Transparent | Transparent | Poorly emulsified | Transparent |

TABLE 1-continued

| | Sample | | | | |
|---|---|---|---|---|---|
| | 1 | 2 | 3 | 4 | 5 |
| L value | 88 | 99 | 97 | — | 99 |
| Stability (at RT for 1M) | ○ | ○ | ○ | x (Separated) | ○ |

*1: 50 mass % solution of the polymer represented by the following formula in isoparaffin same applies to other tables.

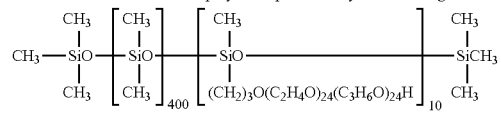

*2: Ethylene Brassylate (INCI name) manufactured by A&E Connock Ltd.; (same applies to other tables).
*3: NISSEKI ISOSOL 400 manufactured by Nippon Oil Corporation (main component is $C_{16}$ isoparaffin).
*4: Syncelan 4 (Nikko Chemicals Co. Ltd.) Its formula is shown below (n = 1 to 3). (same applies to other tables)

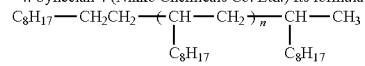

(Production Method)

The components of Parts A were mixed and dissolved with a magnetic stirrer at room temperature to obtain a transparent solution. Separately, the components of Parts B were mixed at room temperature, and then Parts A was added to and mixed with Parts B while stirred with a magnetic stirrer to obtain the desired fragrance composition.

The fragrance compositions were prepared using the composition shown in Table 1. As shown in Sample 2, when only perfume was contained as the oil component, the composition became transparent. This was thought to be because the perfume is an oil component but is ethanol-soluble unlike general oil components such as silicone oils and α-olefin oligomer and thus the perfume dissolved into a large amount of ethanol.

To the contrary, as shown in Sample 1, when silicone oil and α-olefin oligomer were used in combination with perfume, the stable translucent composition could be obtained. When α-olefin oligomer was not used, the appearance of the composition became transparent to fail to obtain the translucent composition, even with other hydrocarbons are used (Samples 3 and 5). When silicone oil was not used, the emulsification was not sufficient to fail to obtain the stable translucent composition (Sample 4).

Then, the present inventors further conducted the study by changing the ratio of α-olefin oligomer/silicone oil.

TABLE 2

| | Sample | | | | |
|---|---|---|---|---|---|
| | 6 | 7 | 8 | 9 | 10 |
| <Parts A> | | | | | |
| Ion exchanged water | 3 | 3 | 3 | 3 | 3 |
| 96% Ethanol | 62 | 62 | 62 | 62 | 62 |
| <Parts B> | | | | | |
| 96% Ethanol | 10 | 10 | 10 | 10 | 10 |
| Polyether-modified silicone *1 | 10 | 10 | 10 | 10 | 10 |
| Perfume*2 | 10 | 10 | 10 | 10 | 10 |
| α-Olefin oligomer*4 | 0 | 1 | 2 | 3 | 4 |
| Dimethylpolysiloxane (6 mPa · s) | 5 | 4 | 3 | 2 | 1 |
| Total | 100 | 100 | 100 | 100 | 100 |
| α-Olefin oligomer/Silicone oil | 0.00 | 0.25 | 0.67 | 1.50 | 4.00 |
| Appearance | Transparent | Translucent | Translucent | Poorly emulsified | Poorly emulsified |
| L value | 97 | 88 | 70 | — | — |
| Stability (at RT for 1M) | ○ | ○ | ○ | x (Separated) | x (Separated) |

The fragrance compositions were prepared using the composition shown in Table 2 by the production method according to Table 1.

As shown in Table 2, when the amount of α-olefin oligomer with respect to silicone oil was too small, there was a case where the composition became transparent. On the other hand, when it was too large, there was a case where the emulsification was insufficient to fail to obtain the stable translucent composition.

From such results, it could be thought that the ratio of α-olefin oligomer/silicone oil is preferably 0.1 to 0.7, and more preferably 0.2 to 0.6.

Then, the present inventors further conducted the study by changing the total amount of α-olefin oligomer and silicone oil.

TABLE 3

| | Sample | | | |
|---|---|---|---|---|
| | 11 | 12 | 13 | 14 |
| <Parts A> | | | | |
| Ion exchanged water | 3 | 3 | 3 | 3 |
| 96% Ethanol | 66 | 62 | 57 | 52 |
| <Parts B> | | | | |
| 96% Ethanol | 10 | 10 | 10 | 10 |
| Polyether-modified silicone *1 | 10 | 10 | 10 | 10 |
| Perfume*2 | 10 | 10 | 10 | 10 |
| α-Olefin oligomer*4 | 0.2 | 1 | 2 | 3 |
| Dimethylpolysiloxane (6 mPa · s) | 0.8 | 4 | 8 | 12 |
| Total | 100 | 100 | 100 | 100 |
| α-Olefin oligomer/Silicone oil | 0.25 | 0.25 | 0.25 | 0.25 |
| Appearance | Transparent | Translucent | Translucent | Poorly emulsified |
| L value | 98 | 88 | 72 | — |
| Stability (at room temperature for 1 M) | ○ | ○ | ○ | x (Separated) |

The fragrance compositions were prepared using the composition shown in Table 3 by the production method according to Table 1.

As shown in Table 3, when the total amount of α-olefin oligomer and silicone oil was too small, there was a case where the composition became transparent. On the other hand, when it was too large, there was a case where the emulsification was insufficient to fail to obtain the stable translucent composition.

From such results, it could be thought that the total amount of α-olefin oligomer and silicone oil is preferably 2 to 12% by mass, and more preferably 4 to 10% by mass, in the composition.

Then, the present inventors further conducted the study by changing the amount of water.

TABLE 4

| | Sample | | | | |
|---|---|---|---|---|---|
| | 15 | 16 | 17 | 18 | 19 |
| <Parts A> | | | | | |
| Ion exchanged water | 0 | 1 | 2 | 10 | 15 |
| 96% Ethanol | 65 | 64 | 63 | 55 | 50 |
| <Parts B> | | | | | |
| 96% Ethanol | 10 | 10 | 10 | 10 | 10 |
| Polyether-modified silicone *1 | 10 | 10 | 10 | 10 | 10 |
| Perfume*2 | 10 | 10 | 10 | 10 | 10 |
| α-Olefin oligomer | 1 | 1 | 1 | 1 | 1 |
| Dimethylpolysiloxane (6 mPa · s) | 4 | 4 | 4 | 4 | 4 |
| Total | 100 | 100 | 100 | 100 | 100 |
| Total amount of water (%) | 3 | 3.96 | 4.92 | 12.6 | 17.4 |
| α-Olefin oligomer/Silicone oil | 0.25 | 0.25 | 0.25 | 0.25 | 0.25 |
| Appearance | Transparent | Slightly translucent | Translucent | Translucent | Milky |
| L value | 98 | 95 | 94 | 73 | 42 |
| Stability (at room temperature for 1 M) | ○ | ○ | ○ | ○ | x (Separated) |

The fragrance compositions were prepared using the composition shown in Table 4 by the production method according to Table 1.

As shown in Table 4, when the amount of water was too small, there was a case where the fragrance composition became transparent. On the other hand, when an excessive amount of water was contained, there was a case where the composition became white like milk or separated.

From such results, it could be thought that the amount of water is preferably 3.5 to 15% by mass, and more preferably 4 to 13% by mass, in the composition.

Then, the present inventors further conducted the study by changing the amount of perfume.

TABLE 5

| | Sample | | | | |
|---|---|---|---|---|---|
| | 20 | 21 | 22 | 23 | 24 |
| <Parts A> | | | | | |
| Ion exchanged water | 3 | 3 | 3 | 3 | 2 |
| 96% Ethanol | 71 | 69 | 62 | 52 | 43 |
| <Parts B> | | | | | |
| 96% Ethanol | 10 | 10 | 10 | 10 | 10 |
| Polyether-modified silicone *1 | 10 | 10 | 10 | 10 | 10 |
| Perfume*2 | 1 | 3 | 10 | 20 | 30 |
| α-Olefin oligomer | 1 | 1 | 1 | 1 | 1 |
| Dimethylpolysiloxane (6 mPa · s) | 4 | 4 | 4 | 4 | 4 |
| Total | 100 | 100 | 100 | 100 | 100 |
| α-Olefin oligomer/Silicone oil | 0.25 | 0.25 | 0.25 | 0.25 | 0.25 |
| Appearance | Milky | Translucent | Translucent | Translucent | Slightly translucent |
| L value | 67 | 85 | 88 | 93 | 95 |
| Stability (at RT for 1 M) | Creaming | ○ | ○ | ○ | ○ |

The fragrance compositions were prepared using the composition shown in Table 5 by the production method according to Table 1.

As shown in Table 5, when the amount of perfume was too small, there was a case where the fragrance composition became white like milk. On the other hand, when the amount of perfume increased, the translucent composition could be obtained, and even 30% by mass of perfume could be contained in the composition. However, as the amount of perfume increased, the tendency that the L value increased and the composition got closer to be transparent was confirmed.

From such results, in the present invention, the amount of perfume is preferably 3 to 30% by, and more preferably 5 to 20% by mass, in the composition.

Then, the present inventors further conducted the study by changing the amount of polyether-modified silicone.

TABLE 6

| | Sample | | | | | | |
|---|---|---|---|---|---|---|---|
| | 25 | 26 | 27 | 28 | 29 | 30 | 31 |
| <Parts A> | | | | | | | |
| Ion exchanged water | 3 | 3 | 3 | 3 | 3 | 3 | 3 |
| 96% Ethanol | 69 | 66 | 62 | 52 | 48 | 49 | 54 |
| <Parts B> | | | | | | | |
| 96% Ethanol | 10 | 10 | 10 | 10 | 10 | 10 | 10 |
| Polyether-modified silicone *1 | 3 | 6 | 10 | 18 | 24 | 15 | 20 |
| Perfume*2 | 10 | 10 | 10 | 10 | 10 | 15 | 3 |
| α-Olefin oligomer*4 | 1 | 1 | 1 | 1 | 1 | 2 | 2 |
| Dimethylpolysiloxane (6 mPa · s) | 4 | 4 | 4 | 4 | 4 | 6 | 8 |
| Total | 100 | 100 | 100 | 98 | 100 | 100 | 100 |
| α-Olefin oligomer/ Silicone oil | 0.25 | 0.25 | 0.25 | 0.25 | 0.25 | 0.33 | 0.25 |
| Modified silicone/ α-Olefin oligomer | 1.5 | 3 | 5 | 9 | 12 | 4 | 5 |
| Appearance | Poorly emulsified | Translucent | Translucent | Translucent | Transparent | Translucent | Translucent |
| L value | — | 86 | 88 | 92 | — | 85 | 78 |
| Stability (at RT for 1M) | x (Separated) | ○ | ○ | ○ | ○ | ○ | ○ |

The fragrance compositions were prepared using the composition shown in Table 6 by the production method according to Table 1.

As shown in Table 6, when the amount of polyether-modified silicone with respect to α-olefin oligomer was too small, there was a case where the emulsification was insufficient to fail to obtain the stable translucent composition. On the other hand, when polyether-modified silicone was contained excessively, there was a case where the composition became transparent.

From such results, it could be thought that the amount of polyether-modified silicone with respect to α-olefin oligomer is preferably 2 to 10 times in mass, and more preferably 3 to 9 times in mass.

Table 7 shows the result of the samples using the same composition with Sample 1 except the kind of perfume. As is clear from Table 7, the stable translucent fragrance composition can be obtained with various kinds of perfumes.

TABLE 7

| | Sample | | |
|---|---|---|---|
| | 32 | 33 | 34 |
| <Parts A> | | | |
| Ion exchanged water | 3 | 3 | 3 |
| 96% Ethanol | 62 | 62 | 62 |
| <Parts B> | | | |
| 96% Ethanol | 10 | 10 | 10 |
| Polyether-modified silicone *1 | 10 | 10 | 10 |
| HEDION*5 | 10 | — | — |
| LINALOOL*6 | — | 10 | — |
| ISO E SUPER*7 | — | — | 10 |
| α-Olefin oligomer*4 | 1 | 1 | 1 |
| Dimethylpolysiloxane (6 mPa · s) | 4 | 4 | 4 |
| Total | 100 | 100 | 100 |
| Appearance | Translucent | Translucent | Translucent |
| L value | 89 | 92 | 87 |
| Stability (at room temperature for 1 M) | ○ | ○ | ○ |

*5Methyldihydrojasmonate (INCI name) manufactured by Firmenich
*6Linalool (INCI name) manufactured by Takasago International Corporation
*7Tetramethyl Acetyloctahydronaphthalenes (INCI name) manufactured by International Flavors & Fragrances Inc.

What is claimed is:

1. A translucent fragrance composition containing:
   (a) a silicone oil;
   (b) α-olefin oligomer that is a hydrogenated trimer, tetramer, pentamer and/or hexamer of α-olefin having 4 to 12 carbons;
   (c) a polyether-modified silicone represented by following formula (1):

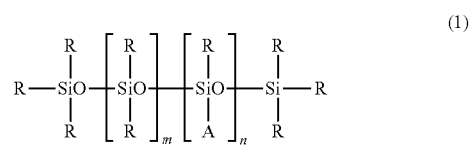

(1)

wherein
A is a polyoxyalkylene group represented by a formula —C$_3$H$_6$O(C$_2$H$_4$O)$_a$(C$_3$H$_6$O)$_b$R', wherein R' is a group selected from a group consisting of a hydrogen atom, an acyl group having 1 to 10 carbon atoms, and an alkyl group having 1 to 4 carbon atoms, a is any integer of 5 to 50, and b is any integer of 5 to 50;
Rs are methyl or phenyl groups;
m is any integer of 50 to 1,000; and
n is any integer of 1 to 40;
   (d) a perfume;
   (e) a lower alcohol having 1 to 4 carbon atoms; and
   (f) water;

wherein
- total amount of (a) silicone oil and (b) α-olefin oligomer is 2 to 12% by mass in the composition, and mass ratio of (b)/(a) is 0.1 to 0.7;
- an amount of (c) polyether-modified silicone with respect to (b) α-olefin oligomer is 2 to 10 times in mass;
- an amount of (d) perfume is 3 to 30% by mass in the composition;
- an amount of (e) lower alcohol is 50% by mass or more in the composition;
- an amount of (f) water is 3.5 to 15% by mass in the composition; and
- an L value of the composition is 70 to 95 provided the L value is a percentage (%) of strength of a transmitted light compared with a strength of an incident light.

2. The translucent fragrance composition according to claim 1, wherein the lower alcohol is ethanol.

* * * * *